United States Patent [19]

Sommer et al.

[11] 4,380,509

[45] Apr. 19, 1983

[54] METHOD FOR PRODUCING A CATALYST FOR THE HYDRATION OF OLEFINS

[75] Inventors: August Sommer; Wilhelm Heitmann, both of Herne; Rainer Brücker, Castrop-Rauxel, all of Fed. Rep. of Germany

[73] Assignee: Chemische Werke Huls AG, Marl, Fed. Rep. of Germany

[21] Appl. No.: 246,257

[22] Filed: Mar. 23, 1981

[30] Foreign Application Priority Data

Mar. 26, 1980 [DE] Fed. Rep. of Germany ....... 3011610

[51] Int. Cl.³ .......................... B01J 37/02; B01J 21/12
[52] U.S. Cl. ................................. 252/453; 252/455 R; 252/458
[58] Field of Search ................... 252/453, 455 R, 435, 252/458; 568/896, 897, 898, 901

[56] References Cited

U.S. PATENT DOCUMENTS

| | | | |
|---|---|---|---|
| 2,162,913 | 6/1939 | Eversole et al. | 568/901 X |
| 3,194,829 | 7/1965 | Moore et al. | 568/897 |
| 3,554,926 | 1/1971 | Statman et al. | 252/435 |
| 3,704,329 | 11/1972 | Rindtorff et al. | 252/435 X |
| 3,989,762 | 11/1976 | Ester | 568/897 |
| 4,038,211 | 7/1977 | Frampton | 252/435 |

Primary Examiner—Carl F. Dees
Attorney, Agent, or Firm—Oblon, Fisher, Spivak, McClelland & Maier

[57] ABSTRACT

A method for producing a carrier for a catalyst comprising the steps of mixing solutions of a soluble salt of aluminum and a soluble salt of silicic acid in a ratio that gives a precipitate comprising aluminum silicate having a weight ratio of $Al_2O_3:SiO_2$ of 1:5 to 1:7, forming the precipitate into a carrier body, consolidating the carrier body by heating, and contacting the carrier body with an acid to reduce the $Al_2O_3$ content to 1–5%. Thus produced carrier bodies are useful for catalyzing the hydration of olefins to alcohols when impregnated with phosphoric acid.

14 Claims, No Drawings

METHOD FOR PRODUCING A CATALYST FOR THE HYDRATION OF OLEFINS

BACKGROUND OF THE INVENTION

1. Field of the Invention

The present invention relates to a catalyst support and more particularly to a catalyst support formed from aluminum silicate which is used, when impregnated with phosphoric acid, as a catalyst for the hydration of olefins.

2. Description of the Prior Art:

It is known that olefins are converted to alcohols by water vapor at high pressure in the gas phase. Such methods have particular technical significance in the production of ethyl alcohol from ethylene and isopropyl alcohol from propylene. The synthesis of these alcohols is carried out in the presence of catalysts. Normally serving as catalyst is phosphoric acid, which is applied to carriers.

Known support materials are either pure silicic acid (e.g. silica gel or infusorial earth) or silicic acid with a more or less large content of alumina, such as calcinized diatomaceous earth, whose structure is held together by clay or other clay-like materials.

With carriers based on silicic acid the stability over longer periods of standing becomes problematic. Materials containing alumina are characterized in particular by better mechanical strength; however, they have the disadvantage that when the alumina content is too high, the aluminum oxide is depleted by the action of the phosphoric acid during the reaction.

A procedure was described in DE-PS No. 11 56 772 for producing a carrier containing alumina for phosphoric acid used as catalyst in olefin hydration in which preformed carrier bodies made of mineral alumina silicates are treated with mineral acid in such a way that the aluminum oxide content is reduced to between 1 and 5% by weight. This material is generally characterized by the necessary mechanical stability as well as by an adequately low residual aluminum oxide content which avoids depletion. On the other hand, when commercially available carrier bodies made of mineral raw materials were used for the production of catalyst supports for the hydration of olefins, it was observed that without previous selection of the raw material, strongly differing catalyst activities were observed.

Finally, carriers were also successfully developed based on large pore silica gel carriers for phosphoric acid with high hydration activity and adequate mechanical strength, e.g. according to DE-OS Nos. 26 25 705 and 27 19 055. However, there is the remaining disadvantage with these carriers based on amorphous silicic acid that when exposed to hydration reaction conditions for long periods, the amorphous silicic acid partially crystallizes into cristobalite and quartz, which is associated with a strong, indeed irreversible, reduction of specific surface and thereby catalytic activity, as well with as a reduction of mechanical strength.

An additional disadvantage of these previously used hydration catalysts based on phosphoric acid applied to silicate carriers is the slow reduction of activity caused by depletion of phosphoric acid. The more recently developed technique of continuously spraying in the depleted amounts of phosphoric acid, according to DE-OS No. 26 58 946, was able to largely eliminate this continuous loss of activity and to considerably increase the life span of the catalysts. This, however, places corresponding demands on the life span of the carrier so that the usefulness of such carriers is determined by crystallization which occurs under reaction conditions and irreversibly reduces catalytic activity and by the mechanical strength which also reduces with time.

According to patent application No. P 29 08 491.1, clay minerals can be used to make a carrier for a hydration catalyst with consistantly high catalytic activity, if care is taken to choose a raw material consisting to a high degree of montmorillonite. The result is that after forming, leaching and impregnating, the active surface on which olefin hydration can occur is large.

Patent application No. P 29 08 491.1 relates to a method for producing a catalyst of clay minerals for the hydration of olefins with 2-3 C-atoms to the corresponding alcohols from phosphoric acid and support materials as well as the thus-produced catalyst. A clay, containing essentially montmorillonite contaminated with no more than 3% accompanying minerals such as quartz, feldspar, and mica, and containing up to 0.5% $K_2O$, is treated in a first step with acid until it has an $Al_2O_3$ content of 13–18% by weight. If necessary, precipitated alumina is added to bring the $Al_2O_3$ content to 16–18% by weight. The resulting material has a surface of 200–400 $m^2/g$, preferably 240–300 $m^2/g$. This is then press formed when its total water content is 20–35%, and calcinated at 500°–800° C. Then the thus formed carrier material is treated in a second step with acid until the $Al_2O_3$ content is 1–5% by weight, preferably 1–3% by weight, whereby a surface of 150–250 $m^2/g$, preferably 180–220 $m^2/g$ is obtained. Finally, the thus obtained carrier is soaked according to known methods in phosphoric acid.

Montmorillonite can be replaced by another mineral of the montmorillonite group containing no potassium, but having the montmorillonite crystalline lattice.

It is also possible to use an acid pre-treated fuller's earth made from a clay with a high montmorillonite content instead of non-acid-treated montmorillonite clay. This eliminates the first acid treatment. This fuller's earth should contain less than 0.1% of $K_2O$; the weight ratio $(Al_2O_3+Fe_2O_3): SiO_2$ should be 1:3.5 to 1:4.5. If necessary, the $Al_2O_3$ content of the fuller's earth can be brought to the necessary 16–18% by weight by adding precipitated alumina.

In comparison to catalysts and catalyst carriers made of preformed carrier bodies based on mineral clay silicates of different origins, the catalysts and carriers produced in this manner have increased activity, i.e. approximately 105–110 g of ethanol or ca. 300 g of isopropyl alcohol are produced per hour and liter of catalyst charge. However, this increased activity can only be maintained over a longer time if the phosphoric acid, depleted at a rate of ca. 0.07 g per hour and liter of catalyst charge with ethanol and 0.01 g per hour and liter of catalyst charge with isopropyl alcohol, is continuously replenished by adding an equal amount of acid.

Patent application No. P 29 29 919.2 deals with a further improvement of the method described above. To the three mentioned raw materials, i.e., either the montmorillonite clay with no more than 3% accompanying minerals such as quartz, feldspar, and mica, having a $K_2O$ content below 0.5, or another mineral of the montmorillonite group containing no potassium, but having the montmorillonite crystalline lattice, or a previously acid-treated fuller's earth, made of clay with a high montmorillonite content, are added 5–15% by weight, based on the total dry substance, of one or more oxides of metals of Group VI of the periodic table before pressing and calcination at 500°–800° C.

With the method according to patent application No. P 29 29 919.2 the following specific improvements are attained:
(a) An increase of the spherical compression strength of the catalyst,
(b) A reduction of phosphoric acid depletion under reaction conditions,
(c) An increase of catalyst activity to ca. 130 g of ethanol per hour and liter of catalyst charge.

SUMMARY OF THE INVENTION

The object of the invention is a method of producing a catalyst for the hydration of olefins with 2–3 C-atoms to the corresponding alcohols, by impregnating a carrier with phosphoric acid, the carrier having been press-formed at a total water content of 20–35%, calcinated at 500°–800° C., and then subjected to an acid treatment to lower the $Al_2O_3$ content to 1–5% by weight, preferably 1–3% by weight, whereby 5–15% by weight, based on the total dry substance, of one or more oxides of metals of Group VI of the periodic table may be added to the carrier before forming in a given case, characterized in that an artificial aluminum silicate obtained by precipitation of soluble salts of aluminum and silicic acid is used as a carrier, whose weight ratio of $Al_2O_3:SiO_2$ is 1:5 to 1:7 and whose specific surface is 350–450 m$^2$/g, and whose specific surface was reduced to 280–380 m$^2$/g and whose pore volume was increased to 1.1 to 1.3 ml/g by acid treatment.

Surprisingly, it was discovered that artificially produced aluminum silicate is superior to natural montmorillonite as a support for hydration catalysts if care is taken in the selection of a high enough concentration of aluminum salt and soluble silicic acid salt so that when precipitating by combining the solutions, a weight ratio of $Al_2O_3:SiO_2$ of 1:5 to 1:7 is present in the insoluble aluminum silicate. In effect, this produces a type of artificial fuller's earth. This concept was used, for example, by N. Nedritsch, Zeitschrift für anorganische Chemie 177 (1929) p. 86. The artificial fuller's earth corresponds to natural fuller's earth in composition, i.e., a montmorillonite after the first treatment step with 20% hydrochloric acid. However, this artificial fuller's earth can be produced with considerably greater specific surface than possible with mineral material after acid treatment, namely 350–450 m$^2$/g compared to 200–400 m$^2$/g, particularly 240–300 m$^2$/g. After forming, calcination, and acid treatment at 100° to 110° C., corresponding to the second acid treatment of the mineral material, the surface of artificial precipitation-produced aluminum silicate regresses only to 280–380 m$^2$/g compared to 150–250 m$^2$/g, particularly 180–220 m$^2$/g, for the mineral material.

According to the method in the invention there is an additional increase in activity of the phosphoric acid impregnated carrier to about 160 g of ethanol and 450 g of isopropyl alcohol per hour and liter of catalyst charge.

The strength of the finished acid-impregnated catalyst is 7–9 kg/body and is adequate for charging common reactors.

As with the mineral montmorillonite, there is an increase in strength with the artificial substance to about 11–13 kg/body, if 5–15%, based on the total dry substance, of an oxide or a mixture of several oxides of elements of Group VI of the periodic table are added before press forming and calcination at 500°–800° C.

Here, too, the depletion of phosphoric acid can be cut in about half, i.e. with ethanol from ca. 0.07 g per hour and liter of catalyst charge to ca. 0.035 g per hour and liter of catalyst charge and with isopropyl alcohol from ca. 0.01 g per hour and liter of catalyst to ca. 0.005 g per hour and liter of catalyst.

Adding oxides of elements of Group VI of the periodic table does not lead to a discernable increase in catalyst activity with the already high initial activity of the carrier of precipitated aluminum silicate.

EXAMPLES

EXAMPLE 1

An artificial aluminum silicate was the precipitate product of a mixture of solutions of aluminum sulfate and sodium silicate in water. The aluminum sulfate contained 16.6 kg of $Al_2(SO_4)_3$ per 100 liters of water, corresponding to 5.0 kg of $Al_2O_3$ per 100 liters of water; the sodium silicate solution contained 48.5 kg of $Na_2SiO_3$ per 100 liters of water, corresponding to 23.8 kg of $SiO_2$ per 100 liters of water. The solutions were combined in the ratio of 5 parts of aluminum sulfate solution to 6 parts of sodium silicate. Thus, after combination the solution contained, per 100 liters of water, 7.5 kg of $Al_2(SO_4)_3$, corresponding to 2.3 kg of $Al_2O_3$, and 26.5 kg of $Na_2SiO_3$, corresponding to 13.0 kg of $SiO_2$. After drying, the resulting precipitate contained 13.2% of $Al_2O_3$ and 86.8% of $SiO_2$; the weight ratio of $Al_2O_3:SiO_2$ was thus 1:6.5.

This material had a specific surface of 387 m$^2$/g and a pore volume of 1.07 ml/g. It was moistened with 43% water, based on the dry substance (that is, 30% water based on the total amount), pressed into cylinders 4 mm in diameter and 4 mm high, and then consolidated by heating for 3 hours at 600° C.

The carrier bodies made in this manner were treated twice for a total of one hour with 20% hydrochloric acid at 100°–110° C. and washed free of acid with water. After drying at about 110°–120° C., an aluminum oxide content of 1.6% was found in the cylinders, the specific surface was 352 m$^2$/g, and the pore volume was 1.18 ml/g. The molded bodies were then covered with a 40% (by weight) solution of phosphoric acid, which was allowed to work for two hours and then they were dried again at ca. 110°–120° C. These thus treated cylinders had an $H_3PO_4$ content of 38% by weight.

A catalyst yield of 160 g of ethanol per hour and liter of catalyst charge could be obtained when hydration catalyst, produced in this manner, was used to synthesize ethanol from ethylene and water in the gas phase under usual conditions.

A catalyst yield of 450 g of isopropyl alcohol per hour and liter of catalyst charge could be obtained when this material was used to synthesize isopropyl alcohol from propylene and water in the gas phase.

The compression strength was 8 kg/body; the acid depletion during operation was 0.07 g per hour and liter of catalyst charge with ethanol and 0.01 g per hour and liter of catalyst charge with isopropyl alcohol.

EXAMPLE 2

An artificial aluminum silicate was produced as a precipitate in a mixture of a solution of aluminum sulfate and sodium silicate in water. The aluminum sulfate solution contained 16.6 kg of $Al_2(SO_4)_3$ per 100 liters of water, corresponding to 5.0 kg of $I_2O_3$ per 100 liters of water; the sodium silicate solution contained 48.5 kg of $Na_2SiO_3$ per 100 liters of water, corresponding to 23.8 kg of $SiO_2$ per 100 liters of water. The solutions were combined in a ratio of 5 parts of aluminum sulfate solution to 6 parts of sodium silicate solution. The resulting solution contained, after combining, per 100 liters of water, 7.5 kg of $Al_2(SO_4)_3$, corresponding to 2.3 kg of $Al_2O_3$ and 26.5 kg of $Na_2SiO_3$, corresponding to 13.0 kg of $SiO_2$. The resulting precipitate contained 13.2% of $Al_2O_3$ and 86.8% of $SiO_2$ after drying; the weight ratio of $Al_2O_3:SiO_2$ was 1:6.5.

This material had a specific surface of 387 $m^2/g$ and a pore volume of 1.07 ml/g. 100 parts of this material were mixed with 3 parts of chromium oxide ($CrO_3$), 3 parts of molybdenum oxide ($MoO_3$), and 5 parts of tungsten oxide ($WO_3$), so that the mixture contained a total of 10% of oxides of elements of group VI of the periodic table. After adding 43% water, based on the dry substance, (that is 30% water based on the total amount) it was pressed into cylinders 4 mm in diameter and 4 mm in height and then consolidated by heating for 3 hours at 600° C.

The carrier bodies made in this manner were treated twice for a total of one hour with 20% hydrochloric acid at 100°–110° C. and washed free of acid with water. After drying at ca. 110°–120° C., an aluminum oxide content of 1.6% was found in the cylinders, the specific surface was 360 $m^2/g$, and the pore volume 1.15 ml/g. The content of oxides of elements of group VI of the periodic table increased to 12% by weight.

The molded bodies were then covered with a 40% by weight solution of phosphoric acid, which was allowed to work for two hours, and then were dried again at about 110°–120° C. These treated cylinders has a $H_3PO_4$ content of 35% by weight.

A catalyst yield of 160 g of ethanol per hour and liter of catalyst charge could be obtained when hydration catalyst, produced in this manner, was used to synthesize ethanol from ethylene and water in the gas phase.

A catalyst yield of 450 g of isopropyl alcohol per hour and liter of catalyst charge could be obtained when this material was used to synthesize isopropyl alcohol from propylene and water in the gas phase.

The compression strength was 12 kg/body; the acid depletion during operation was 0.035 g per hour and liter of catalyst charge with ethanol, and 0.005 g per hour and liter of catalyst charge with isopropyl alcohol.

What we claim is:

1. A method for producing a carrier for a catalyst comprising the steps of:
   mixing a first solution containing a soluble salt of aluminum and a second solution containing a soluble salt of silicic acid in a ratio that gives a precipitate comprising aluminum silicate having a weight ratio of $Al_2O_3:SiO_2$ of 1:5 to 1:7;
   forming said precipitate into a carrier body;
   consolidating said carrier body by heating; and
   treating said carrier body with an acid, wherein the $Al_2O_3$ content of said carrier body is reduced to 1–5% by weight.

2. The method of claim 1, wherein 5–15% of at least one oxide of the Group VI metals is added to said precipitate prior to forming said carrier body.

3. The method of claim 1, wherein said treating reduces the $Al_2O_3$ content to 1–3% by weight.

4. The method of claim 3, wherein said treating reduces the $Al_2O_3$ content to about 1.6% by weight.

5. The method of claim 1, wherein the ratio of $Al_2O_3:SiO_2$ in said precipitate is about 1:6.5.

6. The method of claim 1, wherein said heating is at 500°–800° C.

7. The method of claim 1, wherein the specific surface of said precipitate is 350–450 $m^2/g$.

8. The method of claim 1, wherein said treating reduces the specific surface of said carrier body to 280–380 $m^2/g$.

9. The method of claim 1, wherein said treating increases the pore volume of said carrier body to 1.1 to 1.3 ml/g.

10. The method of claim 1, wherein said carrier body is formed by press-forming.

11. The method of claim 10 wherein the water content of said precipitate is adjusted prior to press-forming.

12. The method of claim 11, wherein said water content is adjusted to 20–35%.

13. The method of claim 1, wherein said acid is hydrochloric acid.

14. The method of claim 1, wherein said soluble salt of aluminum is aluminum sulfate and said soluble salt of silicic acid is sodium silicate.

* * * * *